US008692027B2

(12) United States Patent
Norman et al.

(10) Patent No.: US 8,692,027 B2
(45) Date of Patent: Apr. 8, 2014

(54) CATALYSTS AND PROCESSES FOR PREPARING ALDEHYDES

(75) Inventors: David William Norman, Kingsport, TN (US); Joost Nicolaas Hendrik Reek, Amsterdam (NL); Tatiana Renee Marie-Louise Besset, Amsterdam (NL)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 13/485,033

(22) Filed: May 31, 2012

(65) Prior Publication Data

US 2013/0324767 A1 Dec. 5, 2013

(51) Int. Cl.
C07C 45/50 (2006.01)

(52) U.S. Cl.
USPC .......................................................... 568/454

(58) Field of Classification Search
USPC .......................................................... 568/454
See application file for complete search history.

(56) References Cited

U.S. PATENT DOCUMENTS 5,817,884 A * 10/1998 Bahrmann ..................... 568/454

FOREIGN PATENT DOCUMENTS

| EP | 1 479 439 A1 | 11/2004 |
| EP | 1 888 680 A1 | 2/2008 |
| WO | WO 2008/094222 A2 | 8/2008 |

OTHER PUBLICATIONS

Slagt et al. Encapsulation of Transition Metal Catalysts by Ligand-Template Directed Assemby. Journal of the American Chemical Society, 2004, vol. 126, pp. 1526-1536.*
Kleij et al. Template-Assisted Ligand Encapsulation; the Impact of an Unusual Coordination Geometry on a Supramolecular Pyridylphosphine-Zn (II) porphyrin Assembly. Inorganic Chemistry, 2005, vol. 44, pp. 7696-7698.*
Slagt et al. Fine-Tuning Ligands for Catalysis Using Supramolecular Strategies. European Journal of Inorganic Chemistry, 2007, pp. 4653-4662.*
Adler, Alan D. et al.; "On the Preparation of Metalloporphyrins"; J. inorg. nucl. Chem., vol. 32; 1970; pp. 2443-2445.
Bowen, Richard J. et al.; "Convenient Synthetic Routes to Bidentate and Monodentate 2-, 3- and 4-pyridyl Phosphines: Potentially Useful Ligands for Water-Soluble Complex Catalysts"; Journal of Organometallic Chemistry, vol. 554; 1998; pp. 181-184.
Kamer, Paul C. J. et al.; "Chapter 3 Rhodium Phosphite Catalysts"; Rhodium Catalyzed Hydroformylation; 2000; pp. 35-62.
Kleij, Arjan W. et al.; "Encapsulated Transition Metal Catalysts Comprising Peripheral Zn(II)salen Building Blocks: Template-Controlled Reactivity and Selectivity in Hydroformylation Catalysis"; The Royal Society of Chemistry Communication; 2005; pp. 3661-3663.
Kleij, Arjan W. and Reek, Joost N. H.; "Ligand-Template Directed Assembly: An Efficient Approach for the Supramolecular Encapsulation of Transition-Metal Catalysts"; Chem. Eur. J., vol. 12; 2006; pp. 4218-4227.
Kleij, Arjan W. et al.; "$Zn^{II}$-Salphen Complexes as Versatile Building Blocks for the Construction of Supramolecular Box Assemblies"; Chem. Eur. J. vol. 11; 2005; pp. 4743-4750.
Kleij, Arjan W. et al.; "Template-Assisted Ligand Encapsulation; the Impact of an Unusual Coordination Geometry on a Supramolecular Pyridylphosphine-Zn(II)porphyrin Assembly"; Inorganic Chemistry Communication, vol. 44, No. 22; 2005; pp. 7696-7698.
Kuil, Mark et al.; "High-Precision Catalysts: Regioselective Hydroformylation of Internal Alkenes by Encapsulated Rhodium Complexes"; Journal of American Chemical Society, vol. 128; 2006; pp. 11344-11345.
Meyer, W. H. et al.; "Tri (3-pyridyl) phosphine as amphiphilic ligand in rhodium-catalysed hydroformylation of 1-hexene"; Z. Naturforsch, vol. 62b; 2007; pp. 339-345.
Slagt, Vincent F. et al.; "Assembly of Encapsulated Transition Metal Catalysts"; Angew. Chem. Int. Ed., vol. 40, No. 22; 2001; pp. 4271-4274.
Slagt, Vincent F. et al.; "Encapsulation of Transition Metal Catalysts by Ligand-Template Directed Assembly"; Journal American Chemical Society, vol. 126; 2004; pp. 1526-1536.
Slagt, Vincent et al.; "Fine-Tuning Ligands for Catalysis Using Supramolecular Strategies"; European Journal of Inorganic Chemistry; 2007; pp. 4653-4662.
Van Leeuwen, Piet W. N. M.; "Chapter 1 Introduction to Hydroformylation, Phosphorus Ligands in Homogeneous Catalysis"; Rhodium Catalyzed Hydroformylation; 2000; pp. 1-8.
Van Leeuwen, Piet W. N. M. et al.; "Chapter 4 Phosphines as Ligands, Bite Angle Effects for Diphosphines"; Rhodium Catalyzed Hydroformylation; 2000; pp. 63-105.
Wajda-Hermanowicz, K. et al.; "Rhodium carbonyl complexes of the trans-[RhCl(CO)(PE3)2] type with psyridylphosphines"; Transition Met. Chem., vol. 13; 1988; pp. 101-103.
Co-pending U.S. Appl. No. 13/484,979, filed May 31, 2012; Norman et al.
Co-pending U.S. Appl. No. 13/837,694, filed Mar. 15, 2013; Norman and MacKenzie.
Non-Final Office Action notification date Jul. 17, 2013 received in co-pending U.S. Appl. No. 13/484,979.
Notification of Transmittal of the International Search Report and the Written Opinion of the International Searching Authority, or the Declaration date of mailing Sep. 15, 2013 received in corresponding International Application No. PCT/US2013/042986.
Notification of Transmittal of the International Search Report and the Written Opinion of the International Searching Authority, or the Declaration date of mailing Sep. 16, 2013 received in corresponding International Patent Application No. PCT/US2013/042989.
Notification of Transmittal of the International Search Report and the Written Opinion of the International Searching Authority, or the Declaration date of mailing Sep. 16, 2013 received in corresponding International Patent Application No. PCT/US2013/ 042992.

* cited by examiner

Primary Examiner — Sikarl Witherspoon
(74) Attorney, Agent, or Firm — Ying Yufan Luo

(57) ABSTRACT

Use of a unique supramolecular assembly of a pyridylphosphine ligand and a metal centered porphyrin complex is shown to give unprecedented selectivities to branched aldehydes via rhodium catalyzed hydroformylation of unsubstituted linear alpha-olefins such as propylene and 1-octene. Increasing the syngas pressure is shown to have a beneficial effect on branched aldehyde selectivity as is increasing the ratio of carbon monoxide to hydrogen used in the hydroformylation reaction.

19 Claims, No Drawings

CATALYSTS AND PROCESSES FOR PREPARING ALDEHYDES

BACKGROUND OF THE INVENTION

Iso-Butyraldehyde derivatives are useful solvents and co-monomers in high performance polyesters; however, increasing demands for these materials have created unprecedented challenges for global iso-butyraldehyde production. Hydroformylation, the addition of hydrogen ($H_2$) and carbon monoxide (CO), mixtures of which are known as syngas, to an unsaturated bond is used to produce iso-butyraldehyde from propylene. This process provides a mixture of the linear product, normal-butyraldehyde (N), and the branched, iso-butyraldehyde product (I), with the ratio of normal- to iso-(N:I) typically being greater than or equal to two. The majority of hydroformylation research, particularly within industry, has focused on optimizing the normal aldehyde selectivity while interest in selectively forming the branched aldehyde has only recently emerged. Although an industrially viable process for iso-selective chemistry has yet to be developed, recent academic results have demonstrated highly branched hydroformylation of unsubstituted linear alpha olefins. Selectively hydroformylating at the C2 carbon position of these olefin substrates is quite challenging given that unsubstituted linear alpha olefins bear no discerning electronic or steric features.

To be considered industrially relevant, the turnover frequency of a hydroformylation catalyst system must be at least 1,000 $h^{-1}$. In addition, to avoid costly separation of linear and branched aldehydes from the product stream it would be preferable to generate branched aldehydes in high concentration (>50%). Identifying reaction conditions conducive to achieving N:I ratios below 1.0 from hydroformylation of unsubstituted linear alpha-olefins while obtaining a reaction rate of 1,000 $h^{-1}$ or higher would therefore be desirable.

BRIEF SUMMARY OF THE INVENTION

According to an embodiment, the present invention concerns a process for producing aldehydes, comprising contacting an olefin, with hydrogen and carbon monoxide in the presence of a catalyst composition to produce said aldehydes, wherein the catalyst composition comprises: a mixture of tris(3-pyridyl)phosphine, a metal ion centered tetraphenylporphyrin coordination complex and a rhodium precursor, and wherein the ratio of CO:$H_2$ is from about 4.0:1.0 to about 1.5:1.0.

Another embodiment concerns a process for producing aldehydes, comprising contacting an olefin, with hydrogen and carbon monoxide in the presence of a catalyst composition to produce aldehydes, wherein the catalyst composition comprises the following structure:

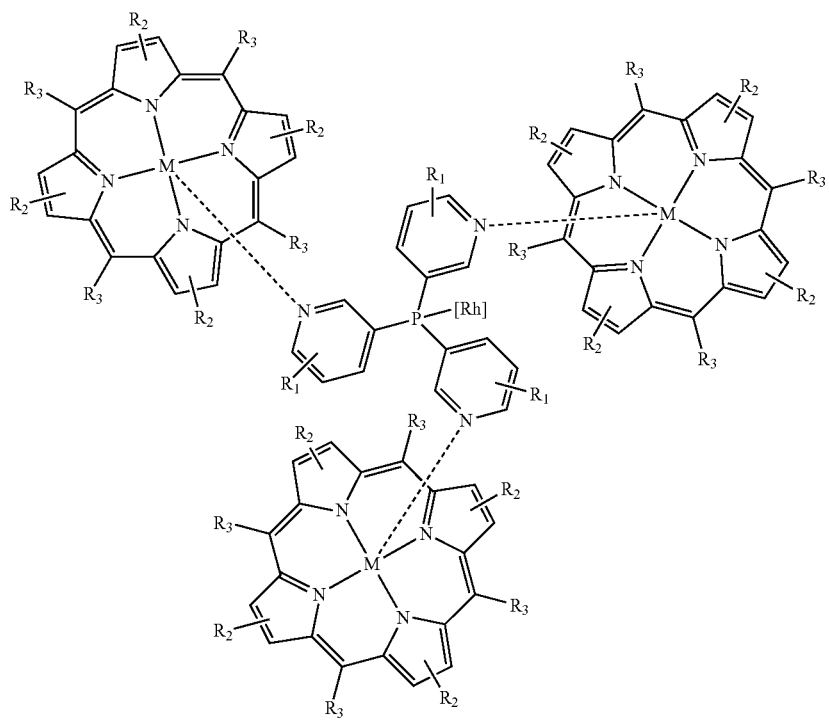

wherein the ratio of CO:$H_2$ is from about 4.0:1.0 to about 1.5:1.0;

wherein M is a metal ion; Rh is a rhodium(I), rhodium(II) or rhodium(III) metal center; $R_1$ is a hydrogen, alkyl, alkoxy, aryl, aryloxy, halogen, nitro group or other heteroatom positioned at a 2, 4, 5 or 6 carbon of each pyridyl ring of the phosphine or any combination thereof; $R_2$ is a hydrogen, alkyl, alkoxy, aryl, aryloxy, halogen, nitro group or other heteroatom positioned at a 2 or 3 carbon position of each pyrrole ring of the porphyrin complex and any combination thereof; and $R_3$ is a hydrogen or phenyl group that may be substituted with an alkyl, alkoxy, aryl, aryloxy, halogen, nitro group or other heteroatom positioned at a 2, 3, 4, 5 and 6 carbon positions of the phenyl ring and any combination thereof.

DETAILED DESCRIPTION

Possessing the ability to produce exclusively iso-butyraldehyde at commercially relevant rates would be a significant achievement for industrial hydroformylation processes. Selective synthesis of normal-aldehydes is relatively straightforward given the advances in ligand design over the past several decades. Efforts to produce the branched isomers from unsubstituted linear alpha olefins, however, have met with little success. In other words, methods for producing normal- to iso-aldehyde mixtures in a 2:1 to 25:1 ratio via rhodium catalysis are well established but industrial technologies for obtaining N:I ratios below 1.2:1 remain in their infancy. For purposes of this invention, N refers to normal (or linear) aldehydes which arise from hydroformylation of the C1 carbon of the olefin substrate and I refers to non-linear aldehydes which arise from hydroformylation of the C2 carbon of the olefin substrate. Moreover, for purposes of the invention, the terminology olefin, olefin substrate and substrate are used interchangeably.

According to an embodiment, the present invention shows that increasing the pressure of equimolar syngas and also the CO partial pressure affords unprecedented branched aldehyde selectivity from the hydroformylation of unsubstituted linear alpha-olefins when the ligand system according to the present invention is employed at elevated reaction temperature. Moreover, a turnover frequency of nearly 3000 $h^{-1}$ is realized when operating under these conditions. The terminology "catalyst ligand system" or "ligand system" is defined as a mixture of tris(3-pyridyl)phosphine (hereafter referred to as "PPy3" or "phosphine ligand" or "ligand" or "phosphine" or "pyridylphosphine") and a metal centered 5,10,15,20-tetraphenylporphyrin coordination complex (hereafter referred to as "tetraphenylporphyrin complex" or "porphyrin complex" or "TPP-M" where M is the metal coordinated by the porphyrin) and a rhodium precursor. Hence, according to an embodiment, a catalyst ligand system according to the present invention has the following structure:

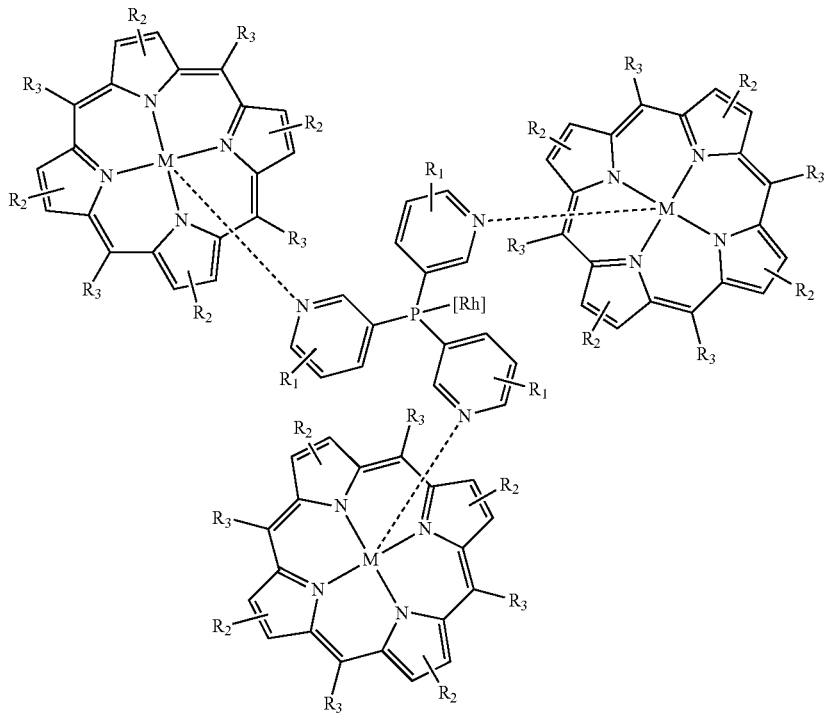

wherein M is a metal ion; [Rh] is a rhodium(I), rhodium(II) or rhodium(III) metal center; $R_1$ is a hydrogen, an alkyl, alkoxy, aryl, aryloxy, halogen, nitro group or other heteroatom positioned at the 2, 4, 5 or 6 carbon position of each pyridyl ring of the phosphine ligand and any combination thereof; $R_2$ is a hydrogen, an alkyl, alkoxy, aryl, aryloxy, halogen, nitro group or other heteroatom positioned at the 2 or 3 carbon position of each pyrrole ring of the porphyrin complex and any combination thereof; $R_3$ is a hydrogen or phenyl group that may be substituted with an alkyl, alkoxy, aryl, aryloxy, halogen, nitro group or other heteroatom positioned at the 2, 3, 4, 5 and 6 carbon positions of the phenyl ring and any combination thereof. The phenyl ring may also be displaced by other aromatic hydrocarbons such as naphthalene, anthracene or partially hydrogenated cyclic aromatic compounds such as tetrahydronaphthalene or octahydroanthracene, each of which may bear any number of substituents such as alkyl, alkoxy, aryl, aryloxy, halogen, nitro or other heteroatom groups. The pyridyl group of the phosphorus ligand may be displaced by other heterocyclic compounds such as quinoline, hydroquinoline, benzoquinoline, hydroisoquinoline, isoquinoline, hydroisoquinoline, benzoisoquinoline or hydrobenzoisoquinoline each of which may bear any number of substituents such as alkyl, alkoxy, aryl, aryloxy, halogen, nitro or other heteroatom groups.

According to an embodiment, the rhodium precursor can be any rhodium containing complex or salt bearing spectator ligands such as, but not limited to, acetylacetonatobis(cyclooctene)rhodium(I); acetylacetonatobis(ethylene)rhodium (I); acetylacetonato(1,5-cyclooctadiene)rhodium(I); bis(1,5-cycloocta-diene)rhodium(I) tetrafluoroborate; bis(1,5-cyclooctadiene)rhodium(I) trifluoromethanesulfonate; bis (norbornadiene)rhodium(I) tetrafluoroborate; chlorobis (cyclooctene) rhodium(I) dimer; chlorobis(ethylene) rhodium(I) dimer; chloro(1,5-cyclooctadiene)rhodium(I) dimer; chlorodicarbonylrhodium(I) dimer; chloronorbornadiene rhodium(I) dimer; dicarbonylacetylacetonato rhodium (I); rhodium(II) acetate dimer; rhodium(III) acetylacetonate; rhodium(III) bromide; rhodium(III) chloride; rhodium(III) iodide; rhodium(II) nitrate; rhodium(II octanoate dimer; rhodium(II) trifluoroacetate dimer; tetrarhodium dodecacarbonyl; di-rhodium tetraacetate dehydrate; rhodium(II) acetate; rhodium(II) isobutyrate; rhodium(II) 2-ethylhexanoate; rhodium(II) benzoate and rhodium(II) octanoate. Also, rhodium carbonyl species such as $Rh_4 (CO)_{12}$ and $Rh_6 (CO)_{16}$ may be suitable rhodium feeds. Additionally, rhodium organophosphine complexes such as tris(triphenylphosphine)rhodium carbonyl hydride may be used when the phosphine moieties of the complex fed are easily displaced by the tris (3-pyridyl)phosphine ligand of the present invention.

According to an embodiment, the catalyst can be prepared by combining a rhodium precursor with tris(3-pyridyl)phosphine and the metal ion centered tetraphenylporphyrin complex in a solvent. Examples of solvents include, but are not limited to, alkanes, cycloalkanes, alkenes, cycloalkenes, carbocyclic aromatic compounds, alcohols, esters, ketones, acetals, ethers and water. Specific examples of such solvents include alkane and cycloalkanes such as dodecane, decalin, octane, iso-octane mixtures, cyclohexane, cyclooctane, cyclododecane, methylcyclohexane; aromatic hydrocarbons such as benzene, toluene, xylene isomers, tetralin, cumene, alkyl-substituted aromatic compounds such as the isomers of diisopropylbenzene, triisopropylbenzene and tert-butylbenzene; crude hydrocarbon mixtures such as naphtha, mineral oils and kerosene; high-boiling esters such as 2,2,4-trimethyl-1,3-pentanediol diisobutyrate. The aldehyde product of the hydroformylation process also may be used. The main criteria for the solvent is that it dissolves the catalyst and olefin substrate and does not act as a poison to the catalyst. Examples of solvents for the production of volatile aldehydes, e.g., the butyraldehydes, are those that are sufficiently high boiling to remain, for the most part, in a gas sparged reactor. Solvents and solvent combinations that are preferred for use in the production of less volatile and non-volatile aldehyde products include 1-methyl-2-pyrrolidinone, dimethylformamide, perfluorinated solvents such as perfluorokerosene, sulfolane, water, and high boiling hydrocarbon liquids as well as combinations of these solvents.

According to an embodiment of the present invention the ratio of $CO:H_2$ can be from about 4.0:1.0 to about 1.5:1.0, or from about 3.5:1.0 to about 1.75:1.0, or even from about 3.0:1.0 to about 2.0:1.0.

According to an embodiment, the present invention concerns a process for producing aldehydes, such as branched aldehydes, comprising contacting an olefin, with hydrogen and carbon monoxide, under hydroformylation conditions to produce aldehydes, in the presence of a catalyst composition comprising tris(3-pyridyl)phosphine, a metal ion centered tetraphenylporphyrin coordination complex and a rhodium precursor.

According to another embodiment, the invention concerns a process for producing aldehydes, such as branched aldehydes, comprising contacting an olefin, with hydrogen and carbon monoxide, under hydroformylation conditions to produce aldehydes, in the presence of a catalyst composition comprising the following structure:

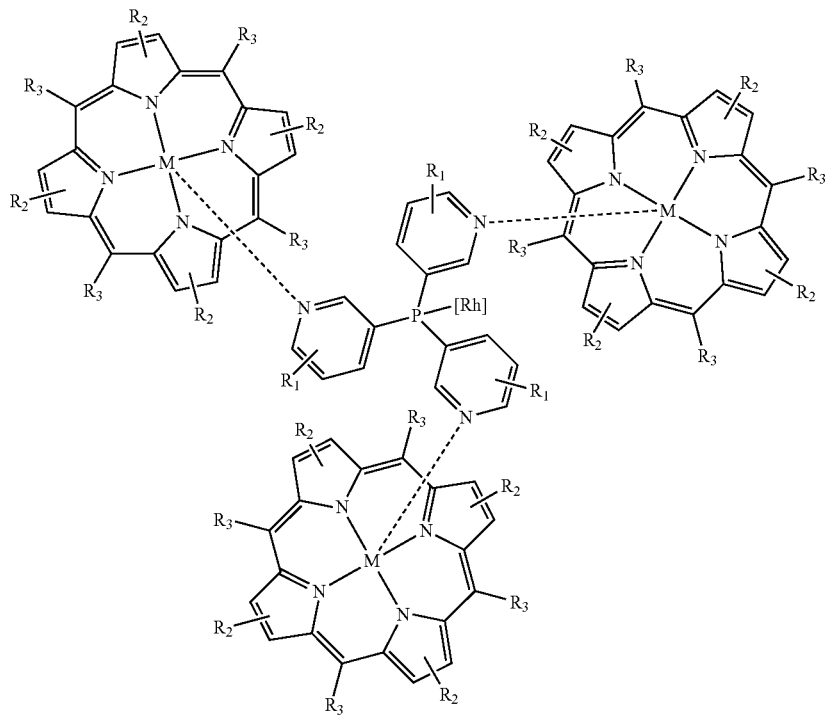

wherein M is a metal ion; [Rh] is a rhodium(I), rhodium(II) or rhodium(III) metal center; $R_1$ is a hydrogen, an alkyl, alkoxy, aryl, aryloxy, halogen, nitro group or other heteroatom positioned at the 2, 4, 5 or 6 carbon position of each pyridyl ring of the phosphine ligand and any combination thereof; $R_2$ is a hydrogen, an alkyl, alkoxy, aryl, aryloxy, halogen, nitro group or other heteroatom positioned at the 2 or 3 carbon position of each pyrrole ring of the porphyrin complex and any combination thereof; $R_3$ is a hydrogen or phenyl group that may be substituted with an alkyl, alkoxy, aryl, aryloxy, halogen, nitro group or other heteroatom positioned at the 2, 3, 4, 5 and 6 carbon positions of the phenyl ring and any combination thereof. The phenyl ring may also be displaced by other aromatic hydrocarbons such as naphthalene, anthracene or partially hydrogenated cyclic aromatic compounds such as tetrahydronaphthalene or octahydroanthracene, each of which may bear any number of substituents such as alkyl, alkoxy, aryl, aryloxy, halogen, nitro or other heteroatom groups. The pyridyl group of the phosphorus ligand may be displaced by other heterocyclic compounds such as quinoline, hydroquinoline, benzoquinoline, hydroisoquinoline, isoquinoline, hydroisoquinoline, benzoisoquinoline or hydrobenzoisoquinoline each of which may bear any number of substituents such as alkyl, alkoxy, aryl, aryloxy, halogen, nitro or other heteroatom groups.

According to an embodiment of this invention the mole ratio of metal porphyrin complex to tris(3-pyridyl)phosphine can be from about 1,000:1 to 3:1 or from about 500:1 to about 100:1 or even from about 10:1 to about 3:1. The mole ratio of tris(3-pyridyl)phosphine ligand to rhodium can be from about 1,000:1 to about 1:1 or from about 500:1 to about 100:1 or even from about 100:1 to about 1:1. The mole ratio of olefin substrate to rhodium can from be about 100,000:1 to about 10:1 or from about 10,000:1 to about 100:1 or even from about 5,000:1 to about 1,000:1. The pressure of the reaction can be from about 345.7 bara (5,000 psig) to about 1.9 bara (1 psig) or from about 69.9 bara (1,000 psig) to about 7.9 bara (100 psig) or even from about 35.5 bara (500 psig) to about 14.8 bara (200 psig). The temperature of the reactor can be from about 500° C. to about 0° C. or from about 100° C. to about 50° C. or even from about 90° C. to about 70° C. The ratio of carbon monoxide to hydrogen can be from about 100:1 to about 0.1:1 or from about 50:1 to about 10:1 or even from about 2.1:1 to about 1.9:1. The rate of reaction, or turnover frequency, can be from about 1,000,000 $h^{-1}$ to about 100 $h^{-1}$ or from about 100,000 $h^{-1}$ to about 1,000 $h^{-1}$ or even from about 10,000 $h^{-1}$ to about 3,000 $h^{-1}$. The N:I ratio of normal-aldehyde product relative to iso-aldehyde product can be from about 2:1 to about 0.01:1 or from about 1.5:1 to about 0.1:1 or from about 1:1 to about 0.25:1.

According to an embodiment, the olefin substrates used in these hydroformylation reactions can be aliphatic, including ethylenically-unsaturated, low molecular weight polymers, alicyclic, aromatic and heterocyclic mono-, di- and triolefins containing up to about 40 carbon atoms. Examples of the aliphatic olefins that may be utilized in the process include straight- and branched-chain, unsubstituted and substituted, aliphatic mono-alpha-olefins containing up to about 20 carbon atoms. Examples of the groups that may be present on the substituted mono-alpha-olefins include hydroxy; alkoxy including ethers and acetals; alkanoyloxy such as acetoxy; amino including substituted amino; carboxy; alkoxycarbonyl; carboxamide; keto; cyano; and the like. Preferred aliphatic mono-alpha-olefins have the general formulas: $H_2C=CH—R_4$ and $H_2C=CH—R_5—R_6$ wherein $R_4$ is hydrogen or straight- or branched-chain alkyl of up to about 8 carbon atoms; $R_5$ is straight- or branched-chain alkylene of up to about 18 carbon atoms; and $R_6$ is hydroxy, alkoxy of up to about 4 carbon atoms, alkanoyloxy of up to about 4 carbon atoms, carboxyl or alkoxycarbonyl of 2 to about 10 carbon atoms. Specific examples of the aliphatic mono-alpha-olefins include ethylene, propylene, 1-butene, 1-pentene, 1-hexene, 1-heptene, 1-octene, 1-nonene, 1-decene, 1-undecene, 1-dodecene, allyl alcohol and 3-acetoxy-1-propene. The aliphatic, di-olefins may contain up to about 40 carbon atoms. Preferred aliphatic, di-olefins have the general formula: $H_2C=CH—R_7—CH=CH_2$ wherein $R_7$ is straight- or branched-chain alkylene having 1 to about 18 carbon atoms. The cyclic olefins which may be used in the hydroformylation process of the present invention may be cycloalkenes, e.g., cyclohexene, 1,5-cyclooctadiene, and cyclodecatriene, and from various vinyl-substituted cycloalkanes, cycloalkenes, heterocyclic and aromatic compounds. Examples of such cyclic olefins include 4-vinylcyclohexene, 1,3-cyclohexadiene, 4-cyclohexene-carboxylic acid, methyl 4-cyclohexene-carboxylic acid, 1,4-cyclooctadiene and 1,5,9-cyclododecatriene.

According to an embodiment, the metal porphyrin complex is comprised of at least a 5,10,15,20-tetraphenylporphyrin moiety bound to a metal ion or metal ion complexes wherein the metal ion is selected from the elements found in groups 1 to 12 of the periodic table of the elements. For example, the metal ion (M) could be derived from the following elements: Mg, Ca, V, Cr, Mn, Fe, Co, Ni, Cu, Zn, Rh, Ru, Ir. The metal ion complex could be carbonyl, acetate, acetylacetonoate, or halide derivatives of the metal ions selected from the elements found in groups 1 to 12 of the periodic table of the elements such as V(III)(acetylacetonate), Mn(III)(acetate), Ru(II)(CO), Rh(III)Cl, Ir(III)(Cl). The tetraphenylporphyrin fragment may bear functionalized phenyl rings in order to change the steric and electronic properties of the catalyst. For example, the phenyl groups of the porphyrin moiety may be substituted with one or more methyl groups, methoxy groups or nitro groups at the 2, 3, 4, 5 and 6 carbon positions of the phenyl ring. The phenyl ring may also be displaced by other aromatic cyclic hydrocarbons such as naphthalene, anthracene or partially hydrogenated cyclic aromatic compounds such as tetrahydronaphthalene or octahydroanthracene.

According to an embodiment, the rhodium precursor can be any rhodium containing complex or salt bearing spectator ligands such as, acetylacetonatobis(cyclooctene)rhodium(I); acetylacetonatobis (ethylene)rhodium(I); acetylacetonato(1, 5-cyclooctadiene)rhodium(I); bis(1,5-cycloocta-diene) rhodium(I) tetrafluoroborate; bis(1,5-cyclooctadiene) rhodium(I) trifluoromethanesulfonate; bis(norbornadiene) rhodium(I) tetrafluoroborate; chlorobis(cyclooctene) rhodium(I) dimer; chlorobis(ethylene)rhodium(I) dimer; chloro(1,5-cyclooctadiene)rhodium(I) dimer; chlorodicarbonylrhodium(I) dimer; chloronorbornadiene rhodium(I) dimer; dicarbonylacetylacetonato rhodium(I); rhodium(II) acetate dimer; rhodium(III) acetylacetonate; rhodium(III) bromide; rhodium(III) chloride; rhodium(III) iodide; rhodium(II) nitrate; rhodium(II octanoate dimer; rhodium(II) trifluoroacetate dimer; tetrarhodium dodecacarbonyl; di-rhodium tetraacetate dehydrate; rhodium(II) acetate; rhodium(II) isobutyrate; rhodium(II) 2-ethylhexanoate; rhodium (II) benzoate and rhodium(II) octanoate. Also, rhodium carbonyl species such as $Rh_4 (CO)_{12}$ and $Rh_6 (CO)_{16}$ may be suitable rhodium feeds. Additionally, rhodium organophosphine complexes such as tris(triphenylphosphine) rhodium carbonyl hydride may be used when the phosphine moieties of the complex fed are easily displaced by the tris(3-pyridyl) phosphine ligand of the present invention.

Examples of suitable reactor types include, but are not limited to, stirred tank, continuous stirred tank, and tubular reactors. Any of the known hydroformylation reactor designs or configurations may be used for the hydroformylation reaction to produce the aldehyde hydroformylation product. For example, the process may be conducted in a batchwise manner in an autoclave by contacting the olefin substrate olefin with syngas in the presence of the catalyst compositions described herein. It will be apparent to those skilled in the art that other reactor schemes may be used with this invention. For example, the hydroformylation reaction can be conducted in a plurality of reaction zones, in series, in parallel, or it may be conducted batchwise or continuously in a tubular plug flow reaction zone or series of such zones with recycle of unconsumed feed substrate materials if required. The reaction steps may be carried out by the incremental addition of one of the feed substrate materials to the other. Also, the reaction steps can be combined by the joint addition of the feed substrate materials.

EXAMPLES

This invention can be further illustrated by the following examples of preferred embodiments thereof, although it will be understood that these examples are included merely for purposes of illustration and are not intended to limit the scope of the invention unless otherwise specifically indicated.

Abbreviations:

TON=Turnover number; TOF=Turnover frequency; N=normal-aldehyde; I=iso-aldehyde; acac=acetylacetonate; TPP=Tetraphenylporphyrin (5,10,15,20-Tetraphenyl-21H,23H-porphine); GC=Gas chromatography; S/Rh=Substrate/rhodium, L/Rh=Ligand/rhodium, TPP/L=Tetraphenylporphyrin/ligand, M=the metal bound in the porphyrin complex.

General:

The rhodium precursor, Rh(acac)(CO)$_2$, and 1-octene were purchased from commercial suppliers. Unless otherwise stated, propylene (propene) was delivered quantitatively to the reactors by a Brooks Quantim mass flow controller. The metal porphyrin complexes, denoted as TPP-M, were either purchased from commercial suppliers or prepared according to known procedures. The ligand used in the examples described below is tris(3-pyridyl)phosphine, prepared via adaptation of published procedures:

A solution of 1.6 mol/L butyl lithium in hexanes (65 mL, 104 mmol) and TMEDA (14.2 mL, 94.5 mmol) was stirred in a dry flask under nitrogen for 15 minutes. The mixture was cooled to −72° C. and cold dry diethyl ether (300 mL) was added. The solution was then cooled to −115° C. 3-Bromopyridine (9.7 mL, 100.3 mmol) in 50 mL diethyl ether was added dropwise over 30 minutes keeping the temperature below −100° C. This was followed by the addition of PCl$_3$ (1.68 mL, 19.3 mmol) and after 30 minutes of stirring, a second aliquot of PCl$_3$ (0.72 mL, 1.14 mmol). The mixture was stirred for 2 hours at −100° C. and left to warm to room temperature overnight. The mixture was extracted with degassed water (4×300 mL) and the combined aqueous layers were washed with chloroform (3×400 mL). The combined organic layers were dried over MgSO$_4$ and concentrated to afford 6.65 g of a caramel-colored oil. The oil was purified by silica gel chromatography (column pre-treated with 5% triethylamine/heptane) using 0.5% MeOH/0.5% TEA/heptane to afford 2.9 g (39.6% yield) of a white solid. $^{31}$P NMR (300 MHz, CDCl$_3$) 6-24.46. $^1$H NMR (300 MHz, CDCl$_3$) δ 8.64 (dt, J=4.8, 1.5 Hz, 3H), 8.61-8.52 (m, 3H), 7.71-7.52 (m, 3H), 7.42-7.29 (m, 3H).

Calculations:

Percent conversion=[(amount of octene isomers+amount of products)/(amount of 1-octene fed+amount of internal octene isomers+amount of products)]×100%

Percent isomerization=[(amount of internal octene isomers+amount of 2-propylhexanal+amount of 2-ethylheptanal)/(amount of 2-methyl-octanal+amount of nonanal+amount of internal octene isomers+amount of 2-propylhexanal+amount of 2-ethylheptanal)]×100%

Percent iso-aldehyde=[(amount iso-aldehyde)/(amount iso-aldehyde+amount normal-aldehyde)]×100%

Percent normal-aldehyde=[(amount normal-aldehyde)/(amount normal-aldehyde+amount iso-aldehyde)]×100%

TON=[(moles of desired aldehyde produced)/(moles of Rh(acac)(CO)$_2$)]

TOF=[(moles of desired aldehyde produced)/(moles of Rh(acac)(CO)$_2$)]/hour

Examples 1 and 2

Effect of 83.7 bara (1,200 psig) Equimolar Syngas Pressure Using Metal Porphyrin Complexes with the tris(3-pyridyl)phosphine Rhodium System at 19° C. with 1-octene as the Substrate The hydroformylation reaction in Example 1 was carried out by first dissolving Rh(acac)(CO)$_2$ (7.6 mg, 0.03 mmol) in toluene (45 mL) followed by addition of tris(3-pyridyl)phosphine (16.5 mg, 0.066 mmol) then addition of the tetraphenylporphyrin magnesium complex (121 mg, 0.2 mmol). The solution was then degassed by argon bubbling followed by addition of 1-octene (1.34 g, 12 mmol) and a decane internal standard, both via syringe. The solution was then charged to an autoclave which was then pressurized and vented three times with nitrogen. Stirring was set to 1,000 rpm, the reactor temperature maintained at 19° C. and 83.7 bara (1,200 psig) of a 1:1 CO:H$_2$ gas mixture added. The hydroformylation reaction in Example 2 was carried out as described for Example 1 except that the TPP-Zn complex was used instead of TPP-Mg. The results are summarized in Table 1. In both examples the 83.7 bara (1,200 psig) reactor pressure operating in tandem with the ligand system affords N:I ratios below 0.6. The zinc system gave an N:I of 0.47 (68% iso-aldehyde) while the magnesium system gave an even lower N:I of 0.25 (80% iso-aldehyde). The selectivity imparted by the magnesium system at elevated pressure is the highest reported for rhodium catalyzed hydroformylation of unsubstituted linear alpha olefins and is unexpected since increasing syngas pressure generally has unpredictable effects in many hydroformylation catalyst systems.

TABLE 1

| Example | Press. (bara) | Time (h) | Temp. (° C.) | Substrate | M | S/Rh | L/Rh | TPP/L | Conv. | N:I | % iso- | Isom. |
|---|---|---|---|---|---|---|---|---|---|---|---|---|
| Ex. 1 | 83.7 | 18 | 19 | 1-Octene | Mg | 407 | 2.1 | 3.0 | 51% | 0.25 | 80% | 0% |
| EX. 2 | 83.7 | 18 | 19 | 1-Octene | Zn | 357 | 2.0 | 2.9 | 100% | 0.47 | 68% | 0% |

Examples 3 and 4

Effect of 21.7 Bara (300 psig) Equimolar Syngas pressure using Metal Porphyrin Complexes with the tris(3-pyridyl)phosphine rhodium System at 19° C. with 1-octene as the Substrate The hydroformylation reactions in these examples were carried out as described in Examples 1 and 2 except that the reactor pressure was 21.7 bara (300 psig). The results are summarized in Table 2. These examples demonstrate that operating under a relatively low equimolar syngas pressure (21.7 vs. 83.7 bara) at 19° C. leads to lower branched aldehyde selectivity irrespective of the identity of the metal coordinated within the porphyrin.

TABLE 2

| Example | Press. (bara) | Time (h) | Temp. (° C.) | Substrate | M | S/Rh | L/Rh | TPP/L | Conv. | N:I | % iso- | Isom. |
|---|---|---|---|---|---|---|---|---|---|---|---|---|
| Ex. 3 | 21.7 | 18 | 19 | 1-Octene | Mg | 415 | 2.2 | 3.0 | 63% | 0.35 | 74% | 0% |
| Ex. 4 | 21.7 | 18 | 19 | 1-Octene | Zn | 377 | 2.1 | 2.9 | 98% | 0.61 | 62% | 0% |

Examples 5 and 6

Effect of 83.7 Bara (1,200 psig) Equimolar Syngas Pressure using Metal Porphyrin Complexes with the tris(3-pyridyl)phosphine Rhodium System at 80° C. with 1-octene as the Substrate The hydroformylation reactions in these examples were carried out as described in Examples 1 and 2 except that the autoclave was heated to 80° C. prior to the pressurization step. The results are summarized in Table 3. These examples demonstrate that the 83.7 bara (1,200 psig) reactor pressure affords an N:I ratio as low as 1.15 (47% iso-aldehyde) which is a seven percent improvement over the selectivity obtained at lower pressure, as described in Example 7.

TABLE 3

| Example | Press. (bara) | Time (h) | Temp. (° C.) | Substrate | M | S/Rh | L/Rh | TPP/L | Conv. | N:I | % iso- | Isom. |
|---|---|---|---|---|---|---|---|---|---|---|---|---|
| Ex. 5 | 83.7 | 1 | 80 | 1-Octene | Mg | 382 | 2.2 | 2.9 | 99% | 1.15 | 47% | 6% |
| Ex. 6 | 83.7 | 1 | 80 | 1-Octene | Zn | 439 | 2.2 | 2.8 | 100% | 1.58 | 39% | 5% |

Example 7 and 8

Effect of 21.7 Bara (300 psig) Equimolar Syngas Pressure using Metal Porphyrin Complexes with the tris(3-pyridyl)phosphine Rhodium System at 80° C. with 1-octene as the Substrate The hydroformylation reactions in these examples were carried out as described in Examples 3 and 4 except that the autoclave was heated to 80° C. prior to the pressurization step. After one hour, the autoclave was vented then cooled and the product analyzed by gas chromatography. The results are summarized in Table 4. These examples demonstrate that both the TPP-zinc and TPP-magnesium systems provide an N:I ratio between 1.5 and 1.6 at 80° C. (~40% iso-aldehyde) when a lower equimolar syngas pressure is employed.

TABLE 4

| Example | Press. (bara) | Time (h) | Temp. (° C.) | Substrate | M | S/Rh | L/Rh | TPP/L | Conv. | N:I | % iso- | Isom. |
|---|---|---|---|---|---|---|---|---|---|---|---|---|
| Ex. 7 | 21.7 | 1 | 80 | 1-Octene | Mg | 383 | 2.0 | 3.3 | 99% | 1.52 | 40% | 8% |
| Ex. 8 | 21.7 | 1 | 80 | 1-Octene | Zn | 413 | 2.5 | 2.9 | 99% | 1.58 | 39% | 5% |

Examples 9 and 10

Effect of 83.7 Bara (1200 psig) Equimolar Syngas Pressure using Metal Porphyrin Complexes with the tris(3-pyridyl)phosphine Rhodium System at 19° C. with Propylene as the Substrate The hydroformylation reactions in these examples were carried out as described in Example 1 except that the substrate used was propylene (propene). The temperature of the reactor was 19° C. in Example 9 and 80° C. in Example 10. The results are summarized in Table 5. Increased pressure evidently has little effect on the N:I ratio when the reaction is carried out at 19° C. However, the added pressure does increase the iso-butyraldehyde selectivity when the reaction is performed at elevated temperature. As noted in Example 10, the N:I ratio decreased from 1.63 (Example 13) to 1.28 (63% vs. 44% iso-aldehyde).

TABLE 5

| Example | Press. (bara) | Time (h) | Temp. (° C.) | Substrate | M | S/Rh | L/Rh | TPP/L | Conv. | N:I | % iso- | Isom. |
|---|---|---|---|---|---|---|---|---|---|---|---|---|
| Ex. 9 | 83.7 | 18 | 19 | Propene | Mg | 374 | 2.3 | 2.8 | 81% | 0.58 | 63% | n/a |
| Ex. 10 | 83.7 | 1 | 80 | Propene | Mg | 355 | 2.3 | 2.8 | 100% | 1.28 | 44% | n/a |

Examples 11 and 12

Effect of 21.7 bara (300 psig) Equimolar Syngas Pressure using Metal Porphyrin Complexes with the tris(3-pyridyl)phosphine Rhodium System at 19° C. with Propylene as the Substrate The hydroformylation reactions in these examples were carried out as described in Examples 3 and 4 except that the substrate used was propylene. The magnesium based catalyst afforded an N:I ratio of 0.6 (63% iso-butyraldehyde) while the zinc system gave an N:I of 1.0 (50% iso-butyraldehyde) at 300 psig.

TABLE 6

| Example | Press. (bara) | Time (h) | Temp. (° C.) | Substrate | M | S/Rh | L/Rh | TPP/L | Conv. | N:I | % iso- | Isom. |
|---|---|---|---|---|---|---|---|---|---|---|---|---|
| Ex. 11 | 21.7 | 18 | 19 | Propene | Mg | 401 | 2.1 | 3.0 | 85% | 0.6 | 63% | n/a |
| Ex. 12 | 21.7 | 18 | 19 | Propene | Zn | 396 | 2.2 | 2.9 | 73% | 1.0 | 50% | n/a |

Examples 13 and 14

Effect of 21.7 Bara (300 psig) Equimolar Syngas Pressure using Metal Porphyrin Complexes with the tris(3-pyridyl)phosphine Rhodium System at 80° C. with Propylene as the Substrate The hydroformylation reactions in these examples were carried out as described in Examples 7 and 8 except that the substrate used was propylene. The amount of ligand used in Example 14 was four times the standard amount. The results are summarized in Table 7. These examples demonstrate that there is little difference in iso-butyraldehyde selectivity when the magnesium or zinc TPP systems are employed at 80° C. and 21.7 bara (300 psig) when propene is the substrate.

Examples 15-18

Effect of 2:1 $CO:H_2$ Pressures using the Zinc Porphyrin Complex with the tris(3-pyridyl)phosphine Rhodium System with 1-octene as the Substrate at 80° C.

The hydroformylation reactions in these examples were carried out as described in Example 6 except that the catalyst concentration was diluted by about a factor of twelve and the ligand to rhodium ratio was higher. Also, the reactor pressure was varied in each example. In all examples except Example 18, the reactor was charged with 0.254 g of the zinc porphyrin complex, 5.0 mL of a 0.005 mol/L solution of Rh(acac)(CO)2 in toluene, 6.29 mL of a 0.02 mol/L solution of tris(3-pyridyl)phosphine in toluene and 37.5 mL of a 3.33 mol/L solution of 1-octene in toluene. This mixture gave the following ratios: octene/Rh=5,000, L/Rh=5, TPP-Zn/L=3. The TPP-Zn complex was omitted in Example 18. In all examples the reactor was pressurized and vented three times with nitrogen then twice more with 360 psig 2:1 $CO:H_2$. Stirring was then set to 1,000 rpm and the reactor pressurized to the desired pressure setting with 2:1 $CO:H_2$ and then heated to the desired set point. After sixteen hours, the autoclave was vented and the product analyzed by gas chromatography. The results are summarized in Table 8. These examples demonstrate that the 67% CO concentration is effective for obtaining N:I ratios of less than 1.0 at an elevated reaction temperature. This comes as a surprise given that syngas compositions with other CO concentrations do not necessarily give equally appealing results (see Examples 25-28). The control reaction (Example 18) clearly shows that, even though the 2:1 $CO:H_2$ atmosphere is present, the N:I selectivity from this reaction is more than 2.0 when the porphyrin complex is omitted from the catalyst system. Thus, the added presence of the metal porphyrin complex is necessary to effect N:I selectivities below 1.0 at elevated reaction temperature.

TABLE 7

| Example | Press. (bara) | Time (h) | Temp. (° C.) | Substrate | M | S/Rh | L/Rh | TPP/L | Conv. | N:I | % iso- | Isom. |
|---|---|---|---|---|---|---|---|---|---|---|---|---|
| Ex. 13 | 21.7 | 1 | 80 | Propene | Mg | 358 | 2.2 | 3.0 | 100% | 1.63 | 38% | n/a |
| Ex. 14 | 21.7 | 1 | 80 | Propene | Zn | 374 | 8.0 | 2.9 | 100% | 1.58 | 39% | n/a |

TABLE 8

| Example | Press. CO:H$_2$ | Time (bara) | Temp. (h) | (°C.) | Substrate | M | S/Rh | L/Rh | TPP/L | Conv. | N:I | % iso- | Isom. |
|---|---|---|---|---|---|---|---|---|---|---|---|---|---|
| Ex. 15 | 2:1 | 81 | 16 | 80 | Octene | Zn | 5,000 | 5 | 3 | 99% | 0.91 | 52% | 2% |
| Ex. 18 | 2:1 | 81 | 16 | 80 | Octene | Zn | 5,000 | 5 | 0 | 99% | 2.11 | 32% | 0% |
| Ex. 16 | 2:1 | 161 | 16 | 80 | Octene | Zn | 5,000 | 5 | 3 | 99% | 0.76 | 57% | 0% |
| Ex. 17 | 2:1 | 241 | 16 | 80 | Octene | Zn | 5,000 | 5 | 3 | 99% | 0.75 | 57% | 0% |

Examples 19-24

Effect of 2:1 CO:H$_2$ Pressures using the Zinc Porphyrin Complex with the tris(3-pyridyl)phosphine Rhodium System with 1-octene as the Substrate at 75° C. and 85° C.

The hydroformylation reactions in these examples were carried out as described in Examples 15-17 except that the reaction temperature was set as 75° C. in Examples 19-21 and 85° C. in Examples 22-24. In all examples the reactor was charged with 0.254 g of the zinc porphyrin complex, 5.0 mL of a 0.005 mol/L solution of Rh(acac)(CO)2 in toluene, 6.29 mL of a 0.02 mol/L solution of tris(3-pyridyl)phosphine in toluene and 37.5 mL of a 3.33 mol/L solution of 1-octene in toluene. This mixture gave the following ratios: octene/Rh=5,000, L/Rh=5, TPP-Zn/L=3. The results are summarized in Table 9. These examples demonstrate that the product selectivity imparted by the ligand system is sensitive to subtle changes in reactor temperature.

CO to H$_2$ was varied in each case. The results are summarized in Table 10; data from Example 15 is added for comparison. These examples demonstrate that as the percentage of CO increases from 33% (1:2 CO:H$_2$) to 50% (1:1 CO:H$_2$) the selectivity toward the branched aldehyde changes only slightly. However, as the percentage of CO increases to 67% (2:1 CO:H$_2$) the selectivity toward the branched aldehyde surprisingly increases. As the percentage of CO continues to increase to 75% (3:1 CO:H$_2$) and 80% (4:1 CO:H$_2$) the selectivity toward the branched aldehyde product decreases.

TABLE 9

| Example | Press. CO:H$_2$ | Time (bara) | Temp. (h) | (°C.) | Substrate | M | S/Rh | L/Rh | TPP/L | Conv. | N:I | % iso- | Isom. |
|---|---|---|---|---|---|---|---|---|---|---|---|---|---|
| Ex. 19 | 2:1 | 81 | 16 | 75 | Octene | Zn | 5,000 | 5 | 3 | 99% | 0.81 | 55% | 0% |
| Ex. 20 | 2:1 | 161 | 16 | 75 | Octene | Zn | 5,000 | 5 | 3 | 99% | 0.73 | 58% | 0% |
| Ex. 21 | 2:1 | 241 | 16 | 75 | Octene | Zn | 5,000 | 5 | 3 | 99% | 0.67 | 60% | 1% |
| Ex. 22 | 2:1 | 81 | 16 | 85 | Octene | Zn | 5,000 | 5 | 3 | 99% | 0.94 | 51% | 0% |
| Ex. 23 | 2:1 | 161 | 16 | 85 | Octene | Zn | 5,000 | 5 | 3 | 99% | 0.79 | 56% | 2% |
| Ex. 24 | 2:1 | 241 | 16 | 85 | Octene | Zn | 5,000 | 5 | 3 | 99% | 0.79 | 56% | 1% |

Examples 25-28

Effect of other CO:H$_2$ Compositions using the Zinc Porphyrin Complex with the tris(3-pyridyl)phosphine Rhodium System with 1-octene as the Substrate at 80° C.

The hydroformylation reactions in these examples were carried out as described in Example 15 except that the ratio of

TABLE 10

| Example | CO:H$_2$ | % CO | Press. (bara) | Time (h) | Temp. (°C.) | Substrate | M | S/Rh | L/Rh | TPP/L | Conv. | N:I | % iso- | Isom. |
|---|---|---|---|---|---|---|---|---|---|---|---|---|---|---|
| Ex. 25 | 1:2 | 33% | 81 | 16 | 80 | Octene | Zn | 5,000 | 5 | 3 | 99% | 1.24 | 45% | 5% |
| Ex. 26 | 1:1 | 50% | 81 | 16 | 80 | Octene | Zn | 5,000 | 5 | 3 | 99% | 1.35 | 43% | 8% |
| Ex. 15 | 2:1 | 67% | 81 | 16 | 80 | Octene | Zn | 5,000 | 5 | 3 | 99% | 0.91 | 52% | 2% |

TABLE 10-continued

| Example | CO:H$_2$ | % CO | Press. (bara) | Time (h) | Temp. (° C.) | Substrate | M | S/Rh | L/Rh | TPP/L | Conv. | N:I | % iso- | Isom. |
|---|---|---|---|---|---|---|---|---|---|---|---|---|---|---|
| Ex. 27 | 3:1 | 75% | 81 | 16 | 80 | Octene | Zn | 5,000 | 5 | 3 | 99% | 0.98 | 50% | 9% |
| Ex. 28 | 4:1 | 80% | 81 | 16 | 80 | Octene | Zn | 5,000 | 5 | 3 | 90% | 1.71 | 37% | 35% |

Example 29

Kinetic Analysis of an Octene Hydroformylation Reaction Carried Out Under 2:1 CO:H$_2$ at 80° C.

The hydroformylation reaction in this example was carried out as described in Example 15 (81 bara, 2:1 CO:H$_2$ and 80° C.) except that the reactor contents were sampled over time. The results are summarized in Table 11. This example demonstrates that reactions rates near 3,000 h$^{-1}$ are obtained while maintaining a N:I selectivity below 1.0 when a 67% CO syngas atmosphere is employed with the ligand system under industrially relevant conditions.

TABLE 11

| Time (h) | Conv. | TOF (h$^{-1}$) | N:I | % iso- | Isom. |
|---|---|---|---|---|---|
| 1 | 60% | 2,998 | 0.92 | 52% | 4% |
| 2 | 96% | 1,811 | 0.9 | 53% | 6% |
| 4 | 99% | 76 | 0.88 | 53% | 3% |

Examples 30 and 31

Effect of 2:1 CO:H$_2$ Using the Zinc Porphyrin Complex with the tris(3-pyridyl)phosphine Rhodium System with Propylene as the Substrate at 80° C.

The hydroformylation reactions in these examples were carried out as described for Example 17 except that propylene was used as substrate. About 29 mL of toluene was used instead of the octene solution and about 5.25 g of propylene added via a pressurized blow case. The approximate substrate to rhodium ratio was 5,000, the ligand to rhodium was 5 and the TPP-Zn to ligand ratio was three. The TPP-Zn/L in Example 31 was zero. The results are summarized in Table 12. These examples demonstrate that the combination of a CO-enriched syngas atmosphere with the ligand system is effective for promoting branched selectivity when propylene is used as substrate. The result from Ex. 31 clearly shows the importance of including the porphyrin complex in the reaction system.

TABLE 12

| Example | Press. (bara) | Time (h) | Temp. (° C.) | Substrate | M | S/Rh | L/Rh | TPP/L | Conv. | % iso- | N:I |
|---|---|---|---|---|---|---|---|---|---|---|---|
| Ex. 30 | 241 | 16 | 80 | Propene | Zn | 5,000 | 5 | 3 | 99% | 48% | 1.07 |
| Ex. 31 | 241 | 16 | 80 | Propene | Zn | 5,000 | 5 | 0 | 99% | 40% | 1.51 |

The invention has been described in detail with particular reference to preferred embodiments thereof, but it will be understood that variations and modifications can be effected within the spirit and scope of the invention.

We claim:

1. A process for producing aldehydes, comprising contacting an olefin, with hydrogen and carbon monoxide in the presence of a catalyst composition to produce said aldehydes, wherein the catalyst composition comprises:
   a mixture of tris(3-pyridyl)phosphine, a metal ion centered tetraphenylporphyrin coordination complex and a rhodium precursor, and
   wherein the ratio of CO:H$_2$ from about 3.5:1 to about 1:1;
   wherein the pressure is below 345.7 bara and above 21.7 bara,
   wherein the reactor temperature is between 0 and 40° C. and
   wherein the aldehydes have an N:I ratio of from about 0.6:1 to about 0.1:1.

2. A process according to claim 1, wherein the ratio of CO:H$_2$ is from about 3.5:1.0 to about 1.75:1.0.

3. A process according to claim 2, wherein the ratio of CO:H$_2$ is from about 3.0:1.0 to about 2.0:1.0.

4. The process according to claim 1, wherein the N:I ratio is from about 0.6:1 to about 0.25:1.

5. The process according to claim 1, wherein the olefin is an unsubstituted linear alpha-olefin.

6. The process according to claim 5, wherein the olefin is propylene, 1-butene, 1-pentene, 1-hexene, 1-heptene, 1-octene, 1-nonene, 1-decene, 1-undecene, 1-dodecene or mixtures thereof.

7. The process according to claim 1, wherein a mole ratio of metal ion centered tetraphenylporphyrin coordination complex to tris(3-pyridyl)phosphine is from about 1,000:1 to about 3:1.

8. The process according to claim 1, wherein a mole ratio of tris(3-pyridyl)phosphine ligand to rhodium precursor is from about 1,000:1 to about 1:1.

9. The process according to claim 1, wherein a mole ratio of olefin to rhodium precursor is from about 100,000:1 to about 10:1.

10. A process for producing aldehydes, comprising contacting an olefin, with hydrogen and carbon monoxide in the presence of a catalyst composition to produce aldehydes, wherein the catalyst composition comprises the following structure:

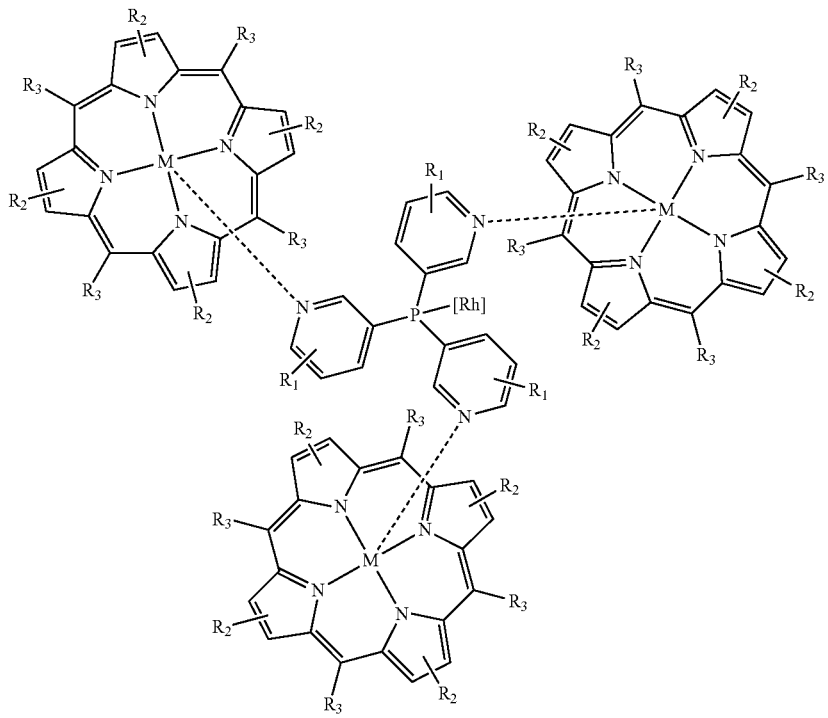

wherein the ratio of CO:H₂ is 1:1; wherein the pressure is below 345.7 bara and above 21.7 bara,
wherein the temperature is between 0-40° C., and
wherein the aldehydes have an N:I ratio of from about 0.6:1 to about 0.1:1;
wherein M is a metal ion;
Rh is a rhodium(I), rhodium(II) or rhodium(III) metal center;
R₁ is a hydrogen, alkyl, alkoxy, aryl, aryloxy, halogen, nitro group or other heteroatom positioned at a 2, 4, 5 or 6 carbon of each pyridyl ring of the phosphine or any combination thereof;
R₂ is a hydrogen, alkyl, alkoxy, aryl, aryloxy, halogen, nitro group or other heteroatom positioned at a 2 or 3 carbon position of each pyrrole ring of the porphyrin complex and any combination thereof; and
R₃ is a hydrogen or phenyl group that may be substituted with an alkyl, alkoxy, aryl, aryloxy, halogen, nitro group or other heteroatom positioned at a 2, 3, 4, 5 and 6 carbon positions of the phenyl ring and any combination thereof.

11. A process according to claim 10, wherein the ratio of CO:H₂ is from about 3.5:1.0 to about 1.75:1.0.

12. A process according to claim 11, wherein the ratio of CO:H₂ is from about 3.0:1.0 to about 2.0:1.0.

13. A process for producing aldehydes, comprising contacting an olefin, with hydrogen and carbon monoxide in the presence of a catalyst composition to produce said aldehydes, wherein the catalyst composition comprises:
a mixture of tris(3-pyridyl)phosphine, a metal ion centered tetraphenylporphyrin coordination complex and a rhodium precursor, and wherein the ratio of CO:H₂ is from about 3.5:1 to about 1.5:1, the CO:H₂ pressure is below 345.7 bara and above 21.7 bara, the reaction temperature is between 75° C. and 85° C. and wherein the aldehydes have an N:I ratio of from about 1.1:1 to about 0.6:1.

14. The process according to claim 13, wherein the olefin is an unsubstituted linear alpha-olefin.

15. The process according to claim 14, wherein the olefin is propylene, 1-butene, 1-pentene, 1-hexene, 1-heptene, 1-octene, 1-nonene, 1-decene, 1-undecene, 1-dodecene or mixtures thereof.

16. The process according to claim 13, wherein a mole ratio of metal ion centered tetraphenylporphyrin coordination complex to tris(3-pyridyl)phosphine is from about 1,000:1 to about 3:1.

17. The process according to claim 13, wherein a mole ratio of tris(3-pyridyl)phosphine ligand to rhodium precursor is from about 1,000:1 to about 1:1.

18. The process according to claim 13, wherein a mole ratio of olefin to rhodium precursor is from about 100,000:1 to about 10:1.

19. A process for producing aldehydes, comprising contacting an olefin, with hydrogen and carbon monoxide in the presence of a catalyst composition to produce aldehydes, wherein the catalyst composition comprises the following structure:

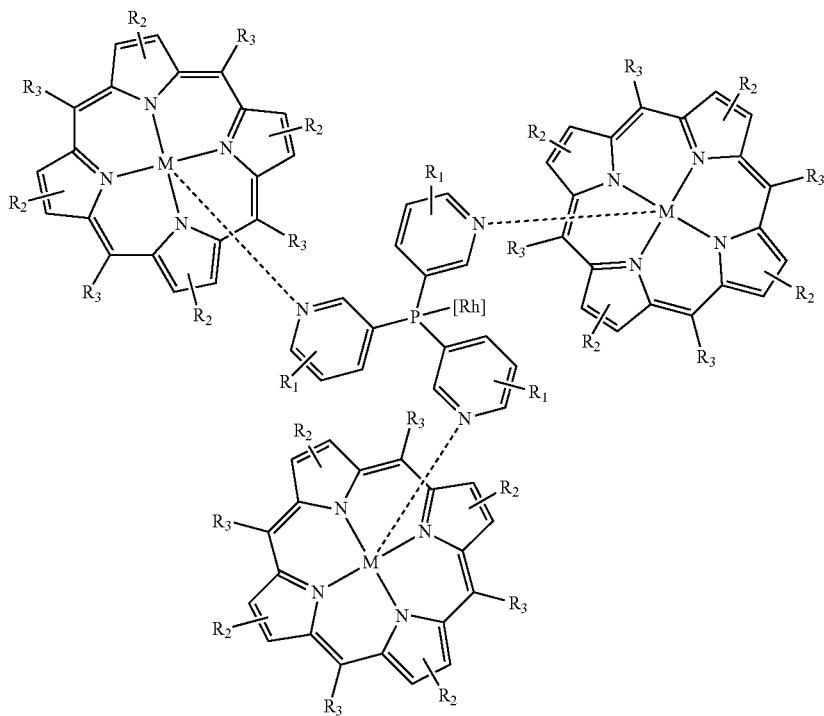

wherein the ratio of $CO:H_2$ is from about 3.5:1 to about 1.5:1, the $CO:H_2$ pressure is below 345.7 bara and above 21.7 bara, the reaction temperature is between 75° C. and 85° C. and wherein the aldehydes have an N:I ratio of from about 1.1:1 to about 0.6:1;

wherein M is a metal ion;

Rh is a rhodium(I), rhodium(II) or rhodium(III) metal center;

$R_1$ is a hydrogen, alkyl, alkoxy, aryl, aryloxy, halogen, nitro group or other heteroatom positioned at a 2, 4, 5 or 6 carbon of each pyridyl ring of the phosphine or any combination thereof;

$R_2$ is a hydrogen, alkyl, alkoxy, aryl, aryloxy, halogen, nitro group or other heteroatom positioned at a 2 or 3 carbon position of each pyrrole ring of the porphyrin complex and any combination thereof; and $R_3$ is a hydrogen or phenyl group that may be substituted with an alkyl, alkoxy, aryl, aryloxy, halogen, nitro group or other heteroatom positioned at a 2, 3, 4, 5 and 6 carbon positions of the phenyl ring and any combination thereof.

* * * * *